(12) United States Patent
Daly

(10) Patent No.: US 10,442,754 B2
(45) Date of Patent: Oct. 15, 2019

(54) MINING COLLECTORS

(71) Applicant: Thomas P. Daly, Arlington Heights, IL (US)

(72) Inventor: Thomas P. Daly, Arlington Heights, IL (US)

( * ) Notice: Subject to any disclaimer, the term of this patent is extended or adjusted under 35 U.S.C. 154(b) by 0 days.

(21) Appl. No.: 15/948,548

(22) Filed: Apr. 9, 2018

(65) Prior Publication Data

US 2018/0222846 A1 Aug. 9, 2018

Related U.S. Application Data

(63) Continuation-in-part of application No. 15/299,816, filed on Oct. 21, 2016, now Pat. No. 10,047,044, which is a continuation of application No. 15/005,162, filed on Jan. 25, 2016, now Pat. No. 9,481,634.

(60) Provisional application No. 62/484,041, filed on Apr. 11, 2017, provisional application No. 62/511,297, filed on May 25, 2017, provisional application No. 62/636,058, filed on Feb. 27, 2018, provisional application No. 62/647,600, filed on Mar. 23, 2018.

(51) Int. Cl.
| | |
|---|---|
| C07C 217/08 | (2006.01) |
| C07C 329/14 | (2006.01) |
| B03D 1/00 | (2006.01) |
| B01F 17/00 | (2006.01) |
| C11D 1/42 | (2006.01) |
| B03D 1/01 | (2006.01) |
| B03D 1/012 | (2006.01) |
| B03D 1/004 | (2006.01) |

(52) U.S. Cl.
CPC ........ *C07C 217/08* (2013.01); *B01F 17/0042* (2013.01); *B03D 1/00* (2013.01); *B03D 1/0043* (2013.01); *B03D 1/011* (2013.01); *B03D 1/012* (2013.01); *C07C 329/14* (2013.01); *C11D 1/42* (2013.01); *C07C 2601/02* (2017.05)

(58) Field of Classification Search
CPC .................................................. C07C 217/08
See application file for complete search history.

(56) References Cited

U.S. PATENT DOCUMENTS

| | | | |
|---|---|---|---|
| 3,135,805 A | 6/1964 | Gilmont | C08F 4/32 260/DIG. 28 |
| 3,449,430 A | 6/1969 | Dohr | A61K 8/40 424/70.19 |
| 4,186,254 A | 1/1980 | Cuscurida | C08G 18/1833 521/115 |
| 5,068,324 A | 11/1991 | O'Lenick, Jr. | A61K 8/84 424/70.21 |
| 6,114,585 A | 9/2000 | Daly | C07C 217/08 564/503 |
| 6,458,999 B1 | 10/2002 | Daly | C07C 217/08 564/348 |
| 9,090,638 B2 | 7/2015 | Daly | C07C 309/14 |
| 2015/0329486 A1 | 11/2015 | Daly | C07D 401/04 560/1 |
| 2016/0052868 A1 | 2/2016 | Daly | C07C 205/15 560/129 |
| 2016/0194283 A1 | 7/2016 | Daly | C07D 213/74 546/312 |
| 2016/0214933 A1 | 7/2016 | Day | |
| 2017/0101371 A1 | 4/2017 | Daly | |

FOREIGN PATENT DOCUMENTS

| | | |
|---|---|---|
| DE | 1 163 850 B1 | 2/1964 |
| JP | H0812983 A | 1/1996 |
| SU | 1489838 A1 | 6/1989 |
| WO | WO2010060477 A | 6/2010 |

OTHER PUBLICATIONS

Lai et al. Polymer Chemistry (2014), 5, 1650.
Xu, et al. Huanjing Huaxue (1988), 7(1), 69-80.
Xu, et al. Huanjing Kexue Xuebao 6(4), pp. 489-507 (1986).
International Search Report and Written Opinion RU PCT/US16/58789 dated Feb. 27, 2017.
PCT Search Rpt and Opiniion, PCT/US18/26738, dated Aug. 30, 2018 (parent case).

*Primary Examiner* — Shawquia Jackson
(74) *Attorney, Agent, or Firm* — Clifford H. Kraft

(57) ABSTRACT

A family of amine mining collectors that uses alkoxylates allows for the easy adjustment of solubility and molecular weight useful because anionic and cationic mineral collectors require such varying degrees of solubility and molecular weight. The family of the present invention allows for the optimization of both parameters and an increase in collector efficiency.

10 Claims, 15 Drawing Sheets

R is chosen from -Si(CH$_3$)$_3$, -Si(CH$_2$)$_m$H, -Si(CH$_2$)$_m$CH$_3$, -H, linear or branched, saturated or unsaturated, cyclic or acyclic from 1 to 22 carbons, R$^1$ is chosen from -H, -OH, -CH$_3$, -CH$_2$CH$_3$. n and m are an integers greater than zero.

R is chosen from -Si(CH$_3$)$_3$, -Si(CH$_2$)$_m$H, -Si(CH$_2$)$_m$CH$_3$, -H, linear or branched, saturated or unsaturated, cyclic or acyclic from 1 to 22 carbons, R¹ is chosen from -H, -OH, -CH$_3$, -CH$_2$CH$_3$. n and m are an integers greater than zero.

Figure 3

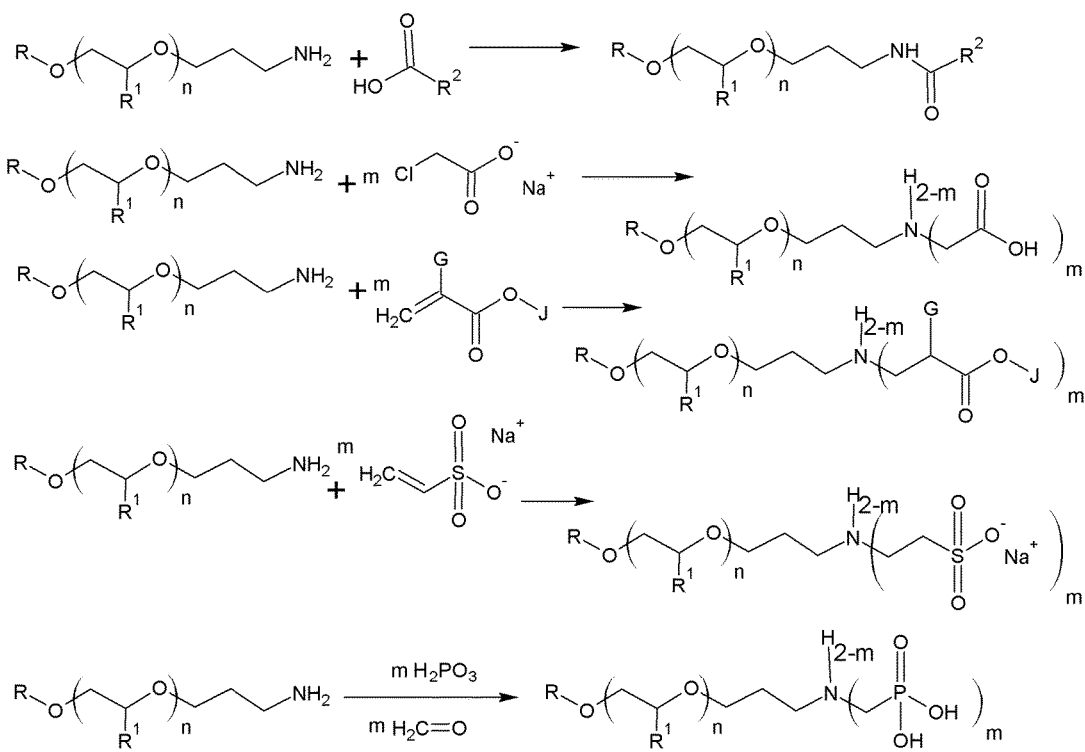

Rand R² are independantly chosen from -Si(CH$_3$)$_3$, -Si(CH$_2$)$_m$H, -Si(CH$_2$)$_m$CH$_3$, -H, linear or branched, saturated or unsaturated, cyclic or acyclic from 1 to 22 carbons, R¹ is chosen from -H, -OH, -CH$_3$, -CH$_2$CH$_3$. n is an integer greater than zero, m is 1 or 2, G is chosen from -H, -OH, -CH2, -CH3, J is chosen from -H, linear or branched, saturated or unsaturated, cyclic or acyclic from 1 to 22 carbons, -(CH2CH2O)xH, -(CH2CH(CH3)O)yH, -(CH2CH(CH2CH3)O)zH, -(CH2CH2O)x-(CH2CH(CH3)O)y-(CH2CH(CH2CH3)O)zH. x,y, and z are integers 0 or greater.

R is chosen from -Si(CH$_3$)$_3$, -Si(CH$_2$)$_m$H, -Si(CH$_2$)$_m$CH$_3$, -H, linear or branched, saturated or unsaturated, cyclic or acyclic from 1 to 22 carbons, R$^1$ is chosen from -H, -OH, -CH$_3$, -CH$_2$CH$_3$. n and m are an integers greater than zero.

R is chosen from -Si(CH$_3$)$_3$, -Si(CH$_2$)$_m$H, -Si(CH$_2$)$_m$CH$_3$, -H, linear or branched, saturated or unsaturated, cyclic or acyclic from 1 to 22 carbons, R$^1$ is chosen from -H, -OH, -CH$_3$, -CH$_2$CH$_3$. n and m are an integers greater than zero.

R is chosen from -Si(CH$_3$)$_3$, -Si(CH$_2$)$_m$H, -Si(CH$_2$)$_m$CH$_3$, -H, linear or branched, saturated or unsaturated, cyclic or acyclic from 1 to 22 carbons, R¹ is chosen from -H, -OH, -CH$_3$, -CH$_2$CH$_3$. n and m are an integers greater than zero.

R is linear or branched, saturated or unsaturated, cyclic or acyclic from 1 to 8 carbons, R $^1$ is chosen from -H, -CH$_3$, -CH$_2$CH$_3$. n is an integer greater than zero such that m+x+y=n.

Figure 8

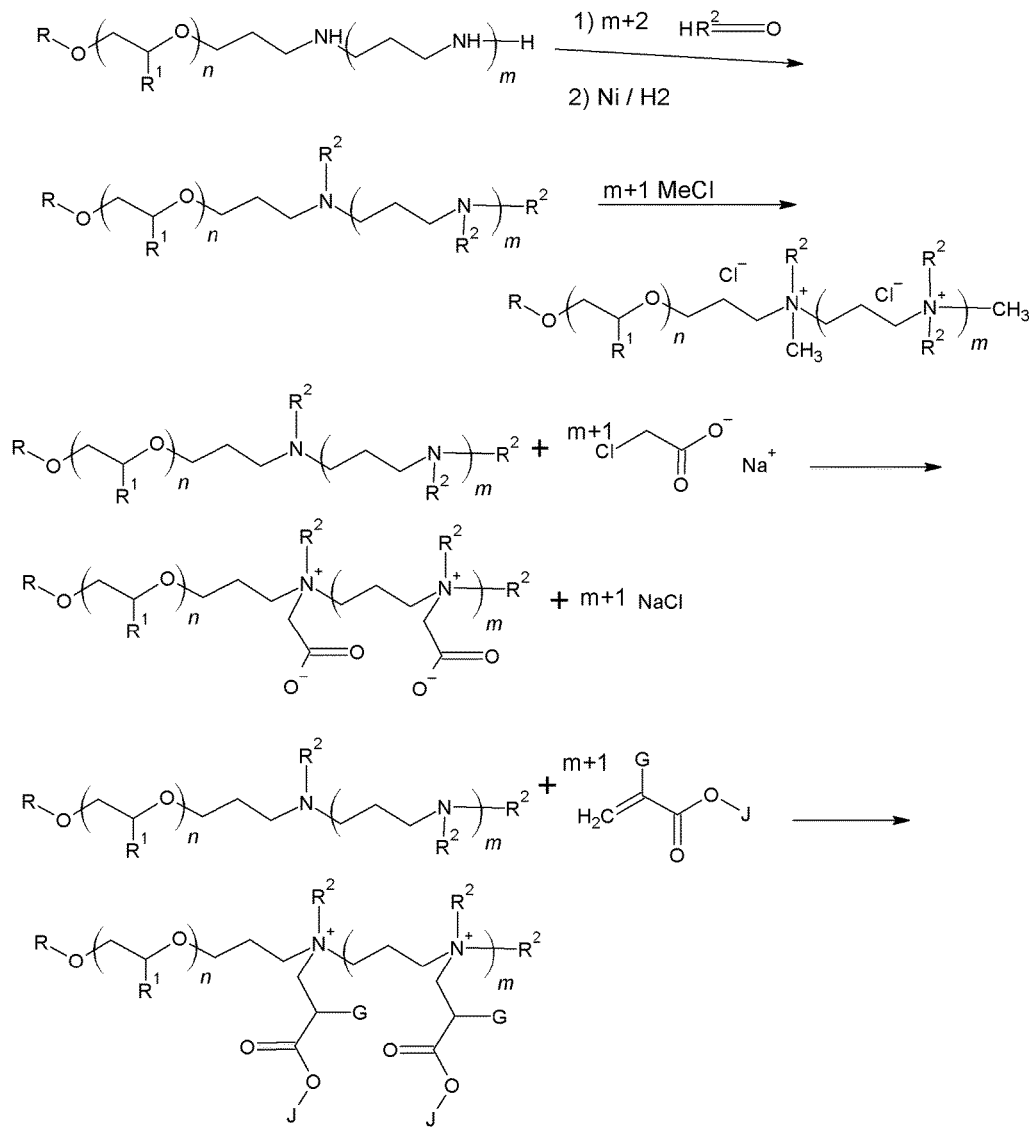

R is chosen from -H, linear or branched, saturated or unsaturated, cyclic or acyclic from 1 to 22 carbons, $R^1$ is chosen from -H, -OH, -CH$_3$, -CH$_2$CH$_3$. $R^2$ is -H, linear or branched, saturated or unsaturated, cyclic or acyclic with one or more carbons. n and m are non-negative integers, q is 1 or 2, G is chosen from -H, -OH, -CH2, -CH3, J is chosen from -H, linear or branched, saturated or unsaturated, cyclic or acyclic from 1 to 22 carbons, -(CH2CH2O)xH, -(CH2CH(CH3)O)yH,-(CH2CH(CH2CH3)O)zH,-(CH2CH2O)x-(CH2CH(CH3)O)y-(CH2CH(CH2CH3)O)zH. x,y, and z are integers 0 or greater.

R is chosen from -OH, linear or branched, saturated or unsaturated, cyclic or acyclic from 1 to 22 carbons, R¹ is chosen from -H, -OH, -CH$_3$, -CH$_2$CH$_3$. R² is linear or branched, saturated or unsaturated, cyclic or acyclic with one or more carbons. n and m are non-negative integers.

Figure 10

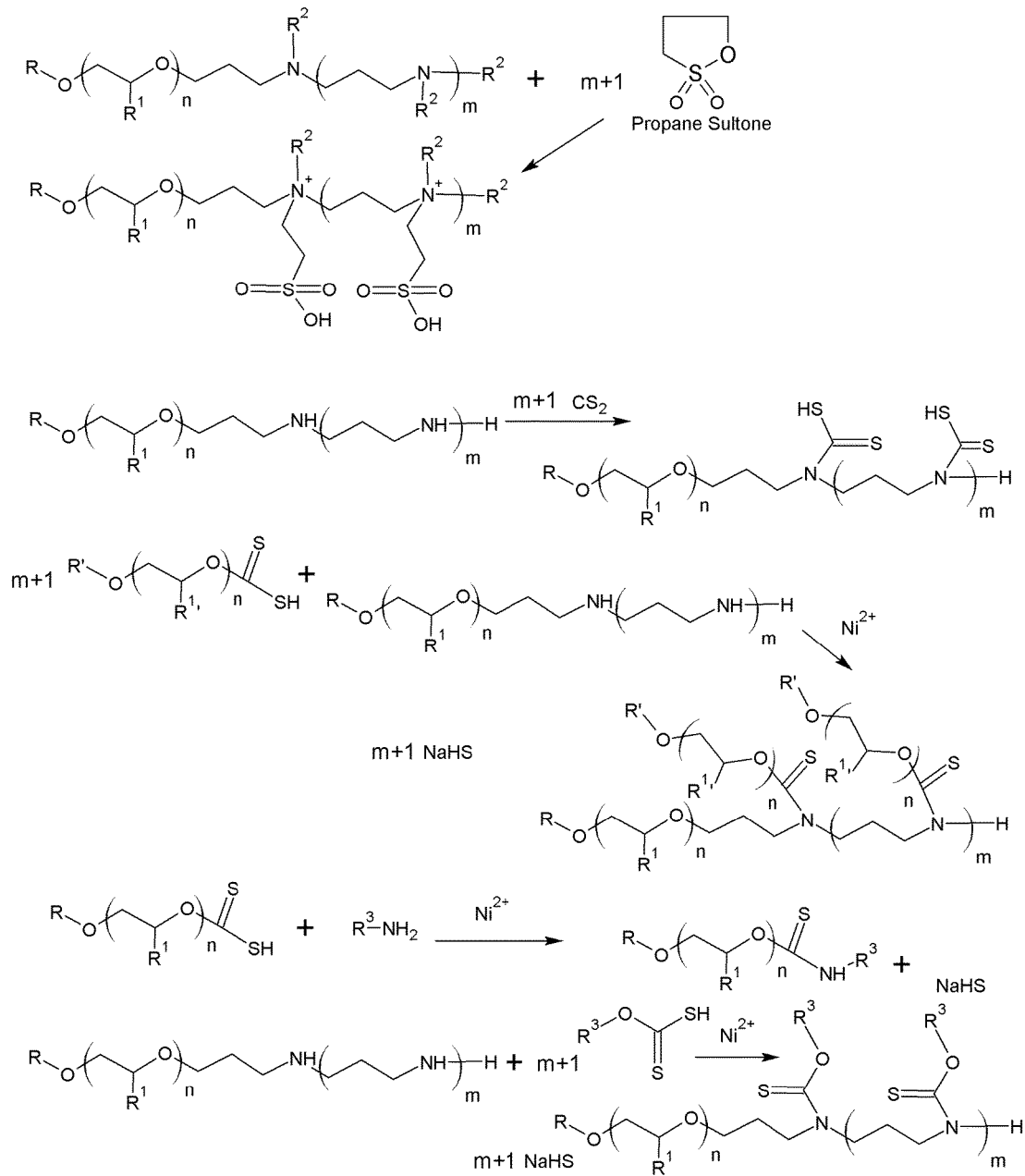

R and R' are independently chosen from -OH, linear or branched, saturated or unsaturated, cyclic or acyclic from 1 to 22 carbons, $R^1$ and $R^{1'}$ are independently chosen from -H, -OH, -$CH_3$, -$CH_2CH_3$. $R^2$ is linear or branched, saturated or unsaturated, cyclic or acyclic with one or more carbons. $R^3$ is linear or branched, saturated or unsaturated, cyclic or acyclic with one or more carbons n and m are non-negative integers.

R is chosen from -OH, linear or branched, saturated or unsaturated, cyclic or acyclic from 1 to 22 carbons, $R^1$ is chosen from -H, -OH, -CH$_3$, -CH$_2$CH$_3$. $R^2$ is linear or branched, saturated or unsaturated, cyclic or acyclic. n and m are non-negative integers..

R[1] is chosen from -H, -CH$_3$, -CH$_2$CH$_3$. n, m and q are integers greater than zero.

R¹ is chosen from -H, -CH$_3$, -CH$_2$CH$_3$. n, m and q are integers greater than zero.

R is chosen from -H, linear or branched, saturated or unsaturated, cyclic or acyclic from 1 to 22 carbons, $R^1$ is chosen from -H, -OH, -$CH_3$, -$CH_2CH_3$. $R^2$ and $R^3$ are independantly chosen from -H, linear or branched, saturated or unsaturated, cyclic or acyclic with one or more carbons. n is a non-negative integer.

Figure 15

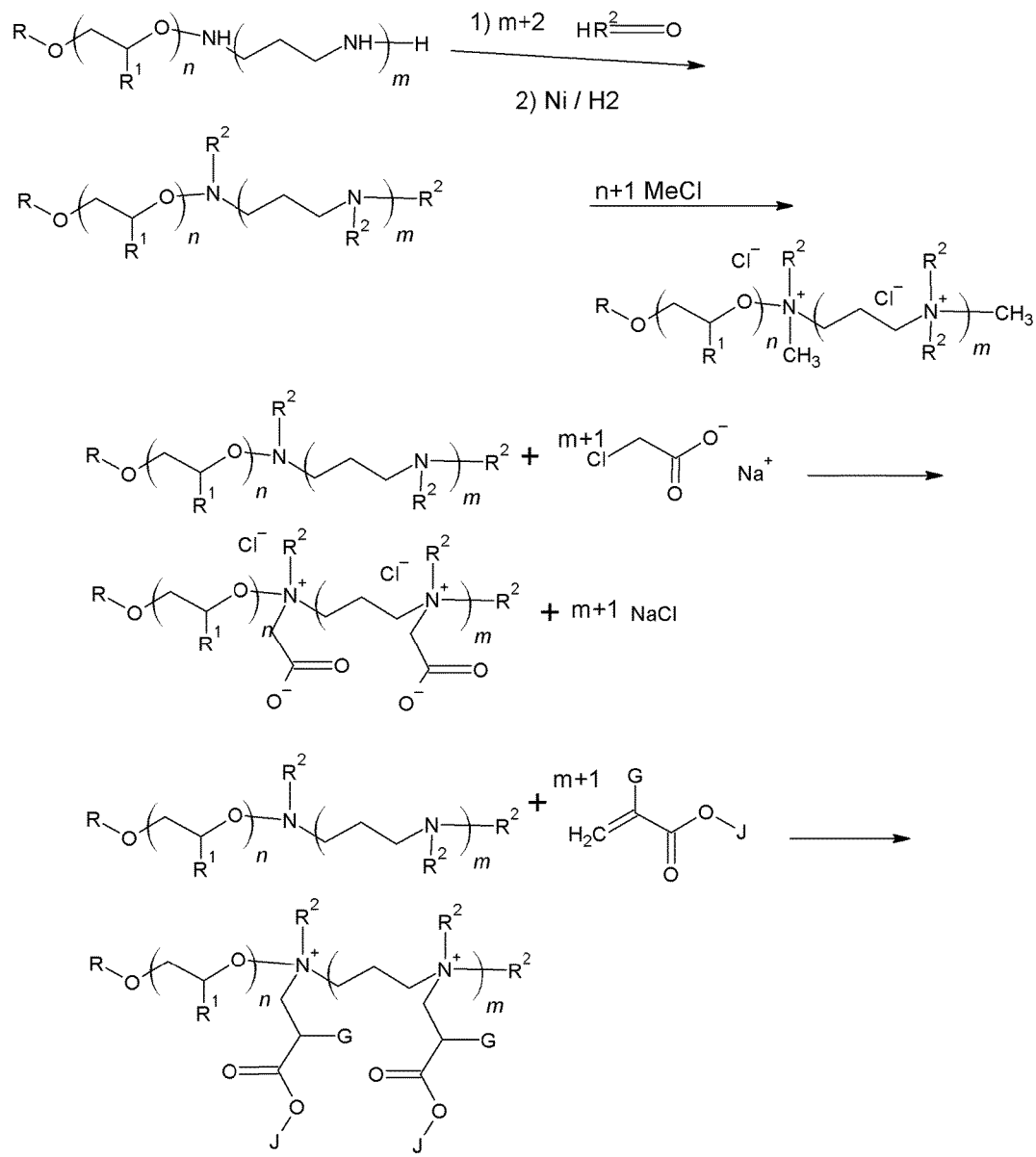

R is chosen from -H, linear or branched, saturated or unsaturated, cyclic or acyclic from 1 to 22 carbons, $R^1$ is chosen from -H, -OH, -CH$_3$, -CH$_2$CH$_3$. $R^2$ is linear or branched, saturated or unsaturated, cyclic or acyclic with one or more carbons. n and m are non-negative integers, q is 1 or 2, G is chosen from -H, -OH, -CH2, -CH3, J is chosen from -H, linear or branched, saturated or unsaturated, cyclic or acyclic from 1 to 22 carbons, -(CH2CH2O)xH, -(CH2CH(CH3)O)yH,-(CH2CH(CH2CH3)O)zH,-(CH2CH2O)x-(CH2CH(CH3)O)y-(CH2CH(CH2CH3)O)zH. x,y, and z are integers 0 or greater.

MINING COLLECTORS

This application is a CIP of Ser. No. 15/299,816 filed Oct. 21, 2016 which was a continuation of Ser. No. 15/005,162 filed Jan. 25, 2016. This application also claims priority from applications 62/484,041, 62/511,297 62/636,058 and 62/647,600. Application Ser. Nos. 15/299,816, 15/005,162, 62/484,041, 61/511,297, 62/636,058 and 62/647,600 are hereby incorporated by reference in their entireties.

BACKGROUND

Field of the Invention

The present invention relates to the field of amine mining collectors and more particularly to a class of ether amines.

Description of the Problem Solved by the Invention

Many commercially important mineral ores are mined from the earth in relatively low concentration. For instance, in Minnesota's Mesabi range, the ore consists of approximately 25% iron. Prior to further processing, the desired minerals must be concentrated. The present invention improves the process of concentrating the desired mineral.

SUMMARY OF THE INVENTION

The present invention relates to the field of amine mining collectors that improve the yield of ore concentration. The use of amines with sufficient water solubility, that form strong water insoluble complexes with the desired mineral, and not with competing minerals results in a higher yield of the desired minerals. The family of amine, xanthate and dithiocarbamate collectors of the present invention does just that.

DESCRIPTION OF THE FIGURES

Attention is now directed to the following figures that describe embodiments of the present invention:

FIG. 3 shows the synthesis of derivatives of the cationic collectors.

FIGS. 8-9 show the synthesis of betaines and polybetaines.

FIG. 10 shows the synthesis of various sulfur derivatives.

FIG. 15 shows the synthesis of the analogous betaines and polybetaines of FIGS. 8 and 9.

DETAILED DESCRIPTION OF THE INVENTION

Mineral ores that are concentrated by floatation are dug out of the ground and ground to a predefined small particle size. The grains of ore are then treated with various surface active molecules and pumped into a floatation pond where dissolved air is introduced. The ore binds to the collector, that creates a water insoluble particle. This water insoluble complex is then floated to the surface by exclusion from the water into the air bubbles that form in dissolved air floatation. Frothers keep a thick head of foam that supports the mineral at the surface until rakes or booms can skim the mineral complex into hoppers for further processing. Ideally, the non target components of the dirt/ore mixture are left to settle to the bottom of the floatation ponds, thus concentrating the desired minerals to an extent that they can then enter the next processing steps, be it reduction, purification or other processing steps.

The present invention utilizes alkoxylates as the backbone of the collector. By varying the side chains on the collector and the chain length, either though increasing the number of repeating units, or by utilizing different chain length or conformations of alcohols to initiate the alkoxylation adjustments to the water solubility, frothing potential and density of the mineral-collector complex can be made. These adjustments allow for the optimization of the collector, by increasing the yield of the target mineral and reducing the collection of non-target minerals, such as silicates.

Figure 1:
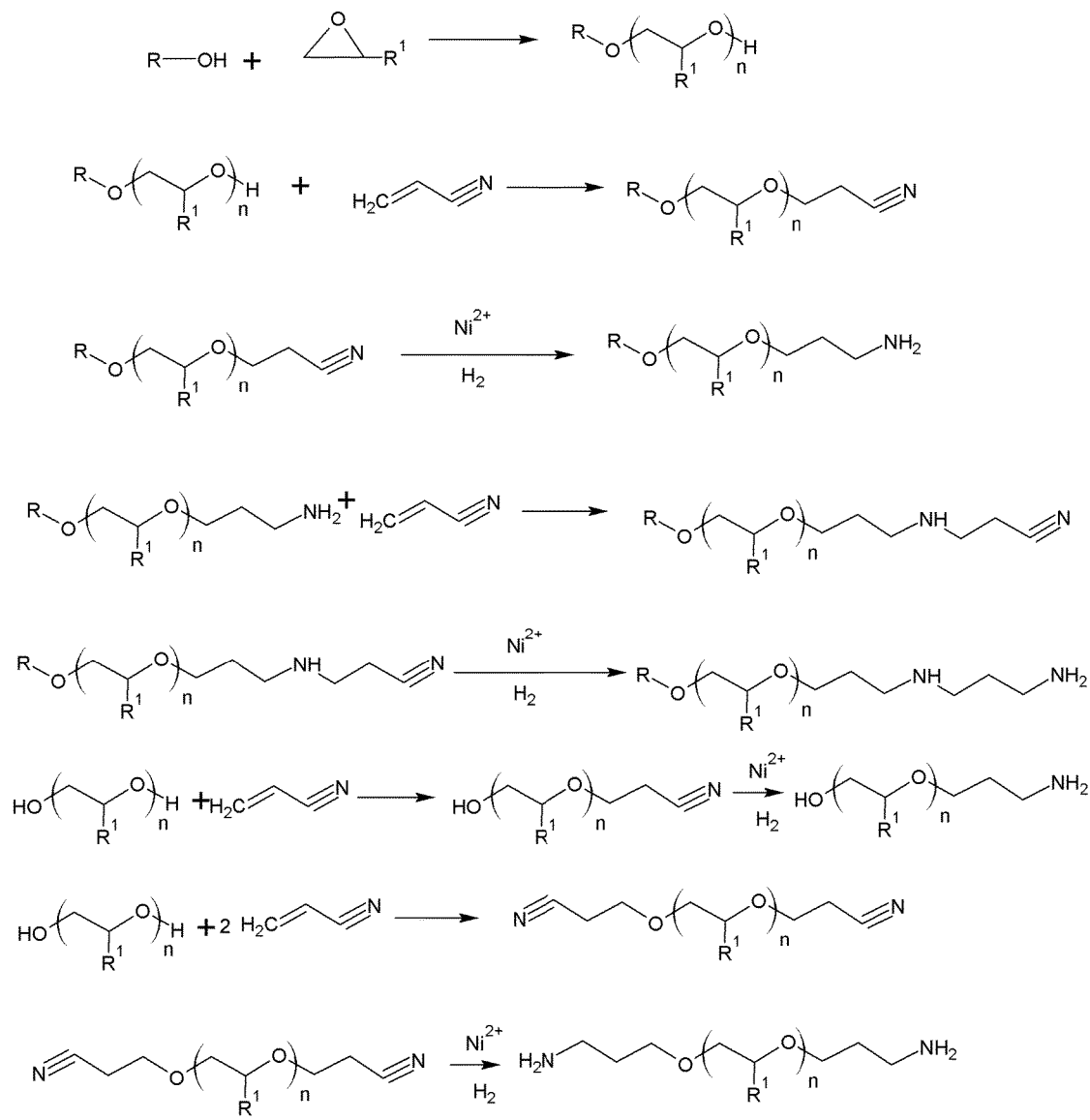
FIG. 1 shows the synthesis of novel ether amine cationic mineral collectors.

FIG. 1 shows the synthesis of primary amine and diamine collectors. The diamines may continue to be sequentially, cyanoethylated to make higher polyamines, such as tri-amines, tetramines and higher. Water is typical used to make polyalkoxylates. The resulting polyalkoxylates have 2 terminal hydroxyls and can react with 2 moles of acrylonitrile to form the di-primary amine. The use of diols and polyols, such as resorcinol, glycerin, neopentyl glycol, and pentaerythritol produce multiple hydroxyls and the analogous products can be formed. The higher polyols beyond diols, introduce branching, which is useful for lower pour points and easier handling, particularly in cold climates. While the figure shows the alkyl portion, R being from 1 to 8 carbons, this is the preferred range for the ore that is mined today. Higher carbon chains show promise in more unusual ores where heavier species are being floated. The invention covers these higher carbon chain analogs as well. This analog holds true for all subsequent figures as well.

Figure 13:
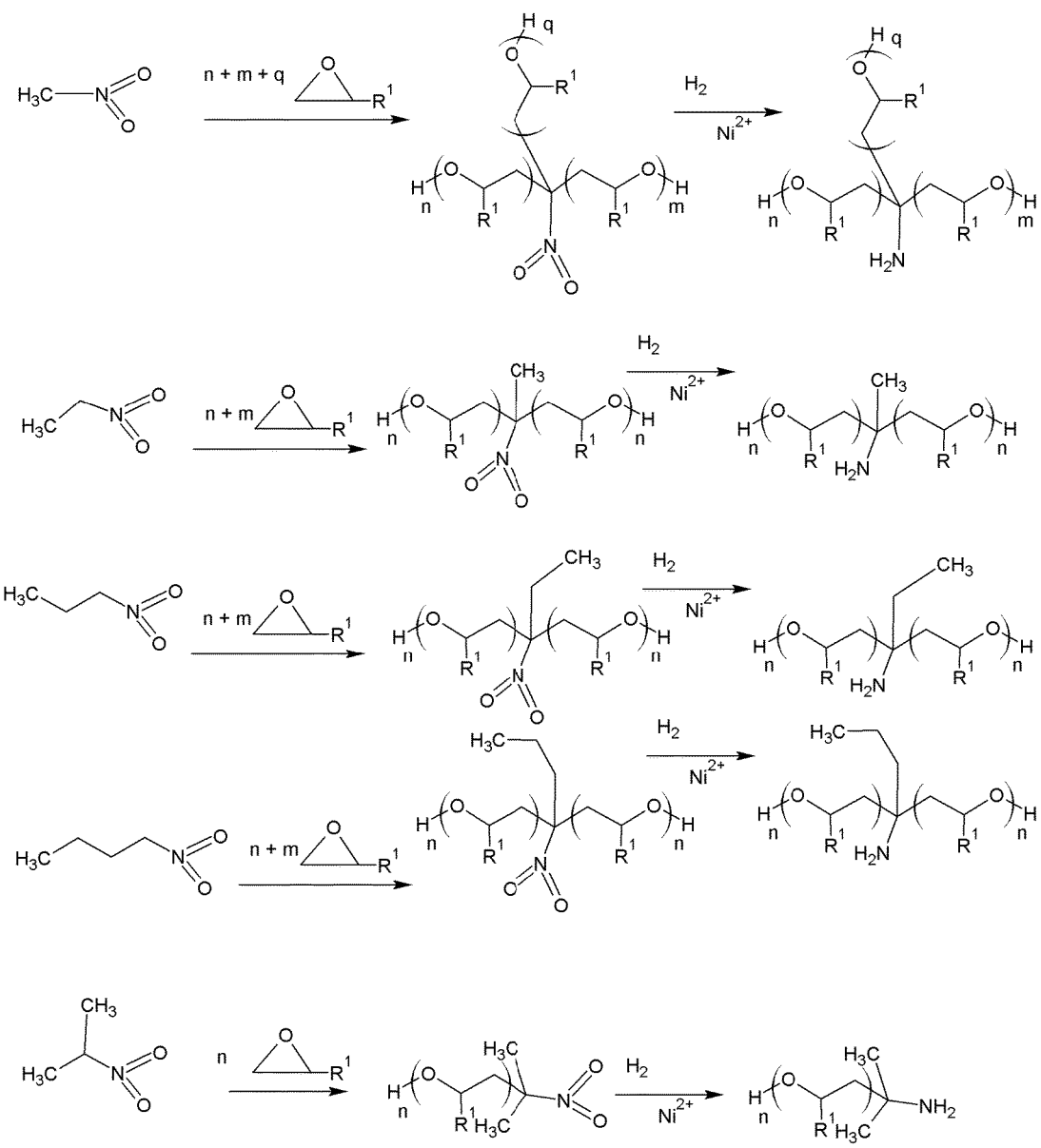

The use of a monohydric alcohol, such as methanol, ethanol, propanol or butanol results in a polyalkoxylate with just one terminal hydroxyl to react the acrylonitrile with, resulting in a primary amine collector. Utilizing higher carbon number alcohols reduces the water solubility of both the collector and the collector-mineral complex. Non-linear alcohols, like phenol, cylcohexanol, isopropanol, or t-butanol reduces the pour point for easier handling in cold climates. Adding a single mole of EO to the starting alcohol, R, when alkoxylating with propylene oxide or butylene oxide reduces the vapor pressure, which helps produce a more even distribution of chain lengths in the alkoxylated alcohol to be either reacted with acrylonitrile as in FIG. 1, or to utilize in direct amination as shown in FIG. 13.

A diamine can also be formed by reacting the previously formed primary amine with an additional mole of acrylonitrile, which is then reduced to form the diamine. This same addition can be done with the primary diamines to yield di-(diamines). The Michael Addition of acrylonitrile to the alcohol and the amine is well known, as is the reduction of the nitrile to the amine with sponge nickel or other sponge metals, either promoted or not, with hydrogen. The reduction typically takes place at a pressure between 400 to 800 psi at less than 40 C over 4 to 12 hours. The Michael Addition is typically done by adding acrylonitrile to the alcohol or amine at ambient temperature with cooling at such a rate as to maintain temperature. Elevated temperatures lead to polymerization of the acrylonitrile. If needed, a catalytic amount of caustic may be used to accelerate the Michael Addition with alcohols. The yields are typically in excess of 96% and no further purification is necessary for a commercial product. These collectors are useful where cationic collectors are required, such as iron ore and potash.

Figure 2:
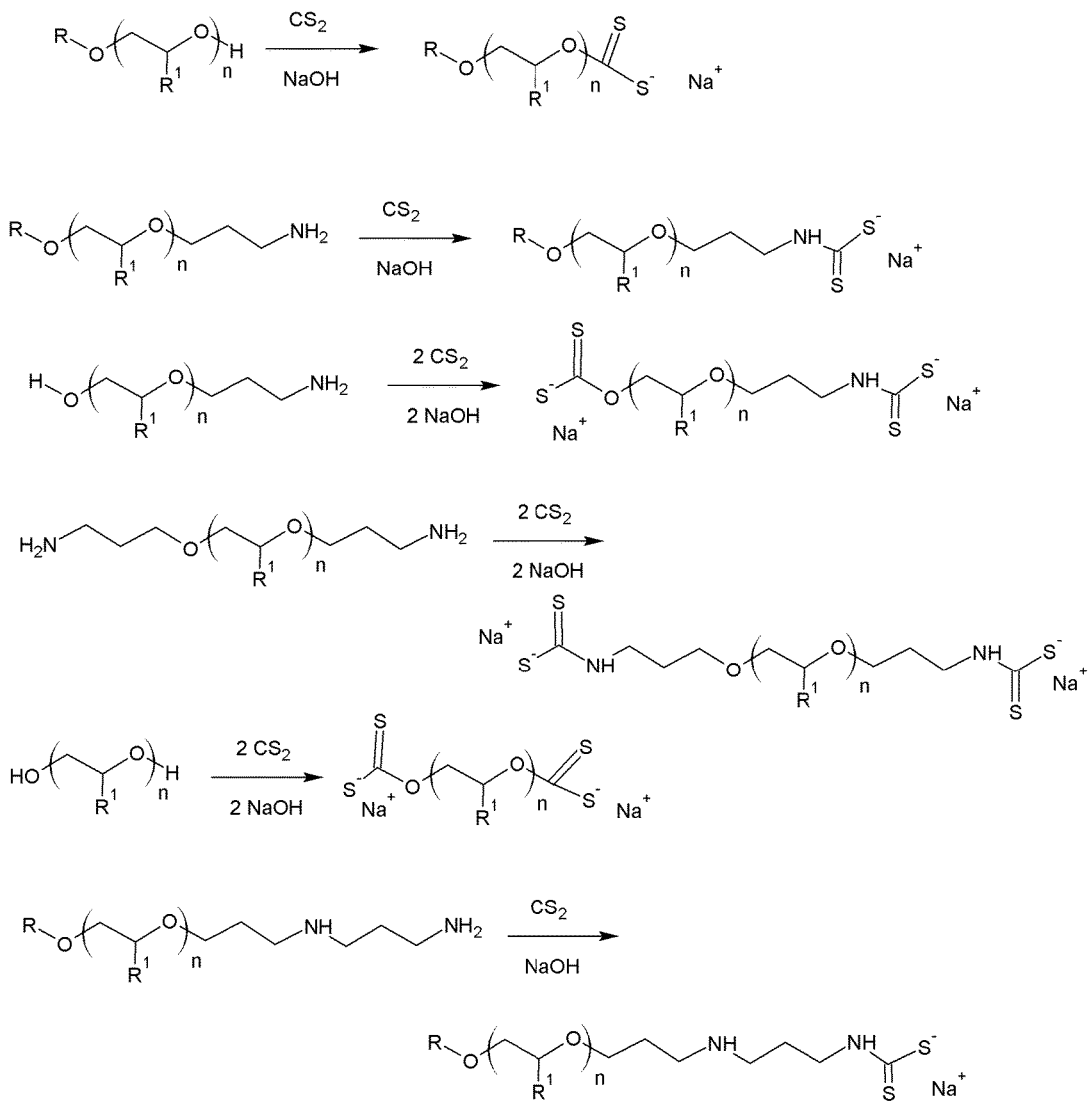
FIG. 2 shows the synthesis of novel anionic mineral collectors.

FIG. 2 shows the synthesis of the anionic analogs of the collectors in FIG. 1. The xanthates and dithiocarbamates. The di-dithiocarbamates may be made from the diamines. The anionic collectors are typically used in sulfide ores. The same solubility trends apply to the anionics as to the cationic collectors of FIG. 1. The xanthates are synthesized by reacting carbon disulfide ($CS_2$) with the alcohol group under basic conditions. The dithiocarbamates are made similarly, but reacting an amino group instead of an alcohol group. The result is a salt of the xanthate or dithiocarbamate. The salt shown in FIG. 2 is always a sodium salt, but any cationic salt is possible and part of the invention. The xanthates and dithiocarbamates can be made as the salts of amines, as well as of mineral bases.

Figure 4:
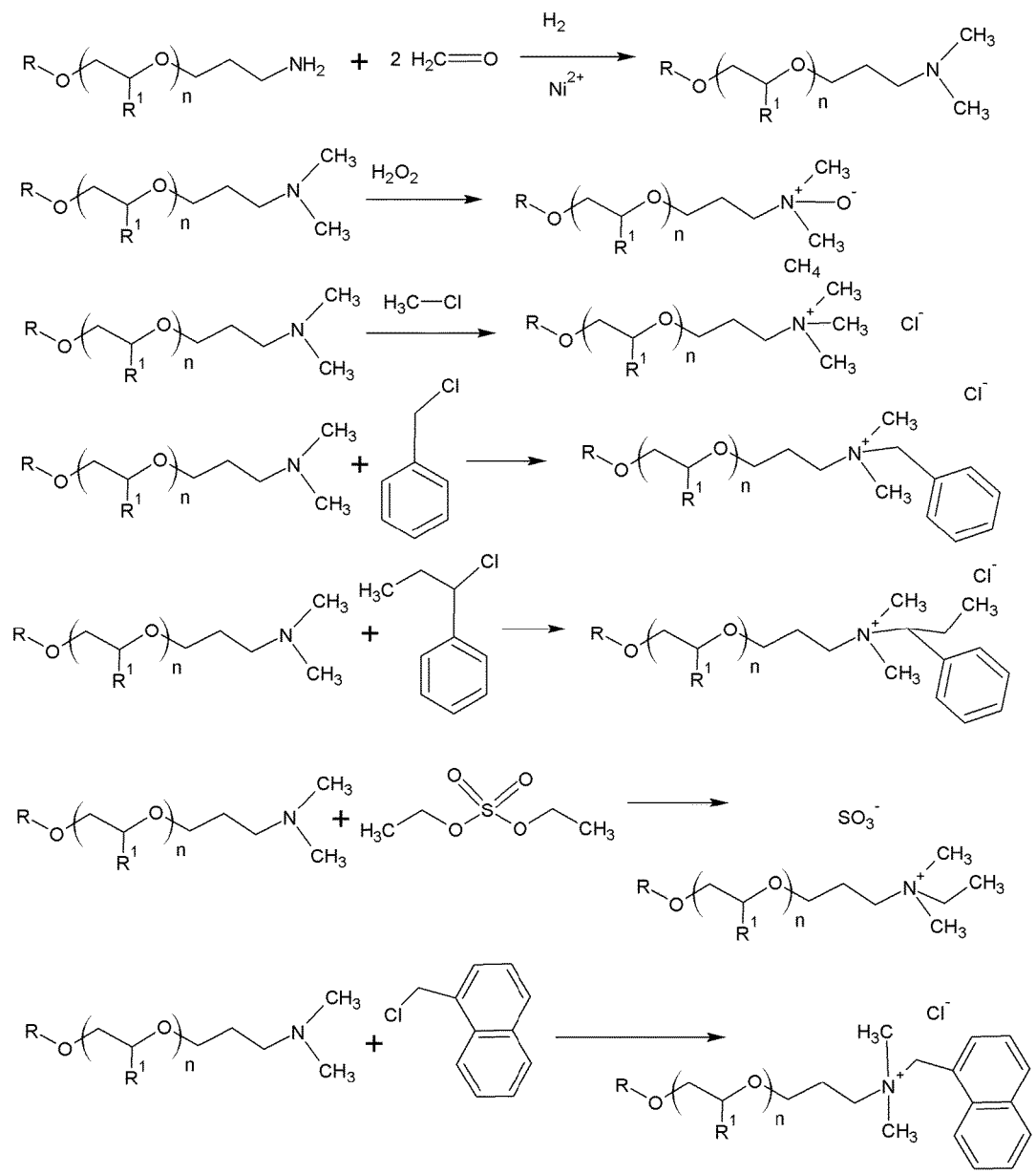
FIG. 4 shows the synthesis of tertiary amine derivatives.

The collectors of the present invention have additional uses as well. The cationic collectors have utility in personal care as surfactants, cleaners, emollients, rheology modifiers, and to buffer the products. The primary amines and diamines also have utility in asphalt as antistrips and as asphalt emulsifiers. FIG. 3 shows several derivatives. Amides with fatty acids of the cationic collectors are made simply by combining the cationic collector with the desired fatty acid, typically stearic acid or coconut fatty acid and heating to remove a mole of water for each amide group formed. The amides are versatile rheology modifiers. Amphoterics of the cationic collectors can be made through the reaction of sodium monochloroacetic acid (reflux 1:1 molar equivalents of SMCA for approximately 8 hours), or for a salt free form, acrylic acid or methacrylic acid may be reacted by adding the acid at ambient temperature or below to the cationic collector with sufficient cooling to keep the temperature below 30 C. The esters can be made by reacting the esters of the acids. A diaddition can be made to the amino group by continuing the reactions. Sulfonates can be made by reacting sodium vinyl sulfonate, propane sultone or butane sultone, or higher sultones can be reacted similarly to create the sulfonates with a longer carbon chain between the nitrogen and the sulfur. Phosphonates can be made by reacting phosphonic acid and formaldehyde. The salted products derivatives of the cationic collectors in FIG. 3 can be in their free form through ion exchange or be salted with any other cation. FIG. 4 shows that tertiary amines can be made by reacting 2 moles of formaldehyde, or other aldehydes, followed by a reduction with sponge nickel under similar conditions to the nitrile reductions in FIG. 1. If different aldehydes are used, an asymmetric tertiary amine results. The tertiary amines can then be made into quaternaries or amine oxides. The quaternaries of methyl chloride, diethylsulfate, ethyl benzyl chloride, and benzyl chloride are all facile reactions at ambient temperature that yield the analogous quaternaries.

Figure 5:
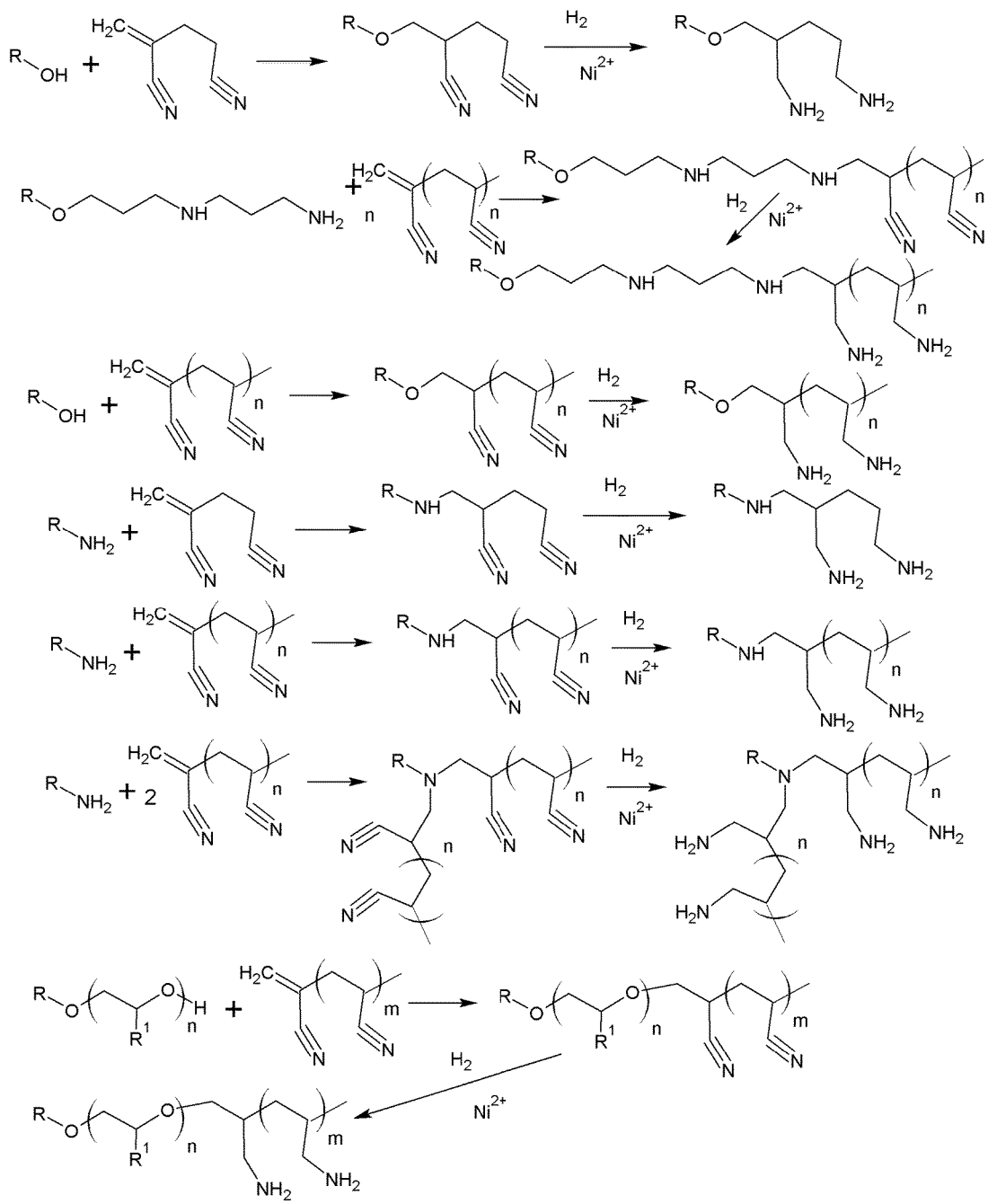
FIG. 5 shows the synthesis of polyprimary amines.

FIG. 5 shows the synthesis of novel collectors based on allylic polynitriles that are then reduced to the polyamines. This unique approach allows for the synthesis of polyprimary amines. The starting material may be an alcohol, an amine, a polyamine such as Tallow Diamine, common trade name Akzo Duomeen T, or polyether amine, such as Air Products DA-14, ethoxylated amines, such as Akzo Ethomeen T12, or ethoxylated ether amines, such as Air Products E-17-5. In the case of primary amines, a second equivalent of the allylic polyacrylonitrile can be added, versus the secondary amines that can only accept one equivalent. Any alcohol or amine functional starting material may be reacted with the allylic polyacrylonitrile and then reduced to form the polyamine is part of this invention.

Figure 6:
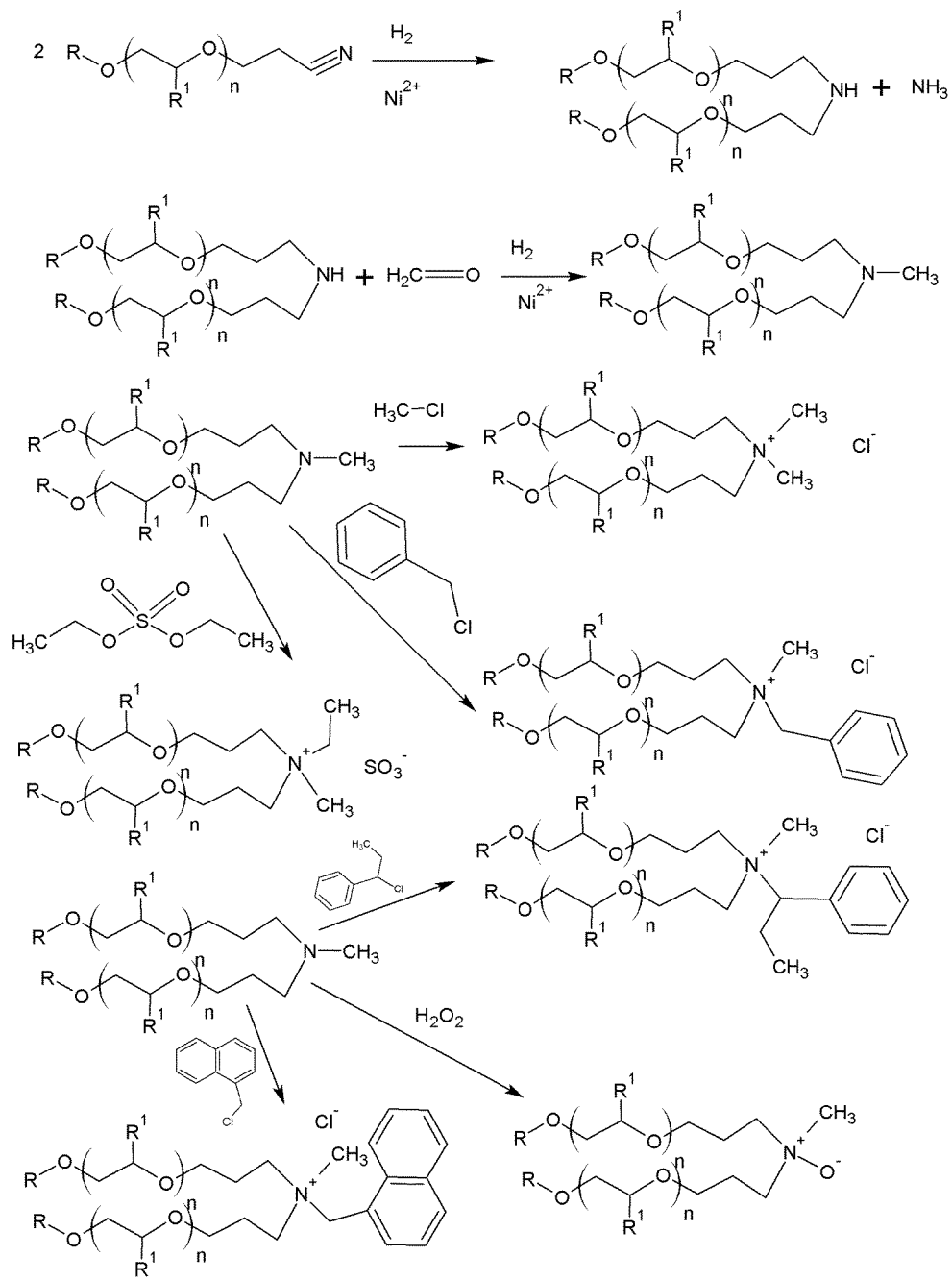
FIG. 6 shows the synthesis of secondary amines and derivatives.

FIG. 6 shows the synthesis of the secondary amines. In FIG. 6, the reactants are 2 moles of the same ether nitrile, but this need not be the case. R and $R^1$ may be different and even a wade range of blends may be used which will give a mixture of symmetric and asymmetric secondary amines. The ether nitriles of the invention may also be reacted alkyl nitriles, such as tallow nitrile, or more conventional ether nitriles, such as the ether nitrile formed by the synthesis of fatty alcohols such as Exxal 10 and acrylonitrile to form asymmetric secondary amines and even the nitriles formed from acrylonitrile and hydroxyl terminated siloxanes or silyl alcohols. The use of differing nitriles allows the chemist to produce secondary amines with a range of hydrophobicities and surfactancies. Conditions for the synthesis are more severe than the synthesis of the primary amines. The reaction generally takes 2 hrs at 220 C, but only about 300 psi pressure of hydrogen. Typical sponge nickel may be used, but beta branched products to appear in larger quantities. A nickel carbonate catalyst will reduce this byproduct formation. While FIG. 6 only shows the synthesis of symmetric secondary amines, the asymmetric secondary amines and their derivatives are part of this invention. The dimethyl quaternary shown in row 3 of FIG. 6 is particularly well suited to treated drilling clays to form hydrophobic clays for use in oilfield drilling muds, as well as biodegradable fabric softeners. These dimethyl quats me be formed as either the sulfate or chloride salt depending on the methylating agent, typically DMS or methyl chloride. The benzyl chloride quats are useful for antimicrobials and corrosion inhibitors. The ethylbenzyl and naphtha quats are anti-fungal as well.

The symmetric tertiary amine of the first row of FIG. 6 is obtained with slightly different conditions. An 85% yield of tertiary amine is obtainable by running the reaction at a lower pressure, ~100 psi, for 4-6 hrs. The corresponding asymmetric tertiary amines can be made by varying the nitriles used as starting materials in the reaction vessel. Similarly, the derivatives, such as amine oxides, and quaternaries analogous to the those shown with the methyl tertiary amine are similarly obtained. The tertiary polyalkoxylate quaternaries are particularly useful as hair conditioners, particularly when a silyl nitrile is used as a starting material.

Figure 7:
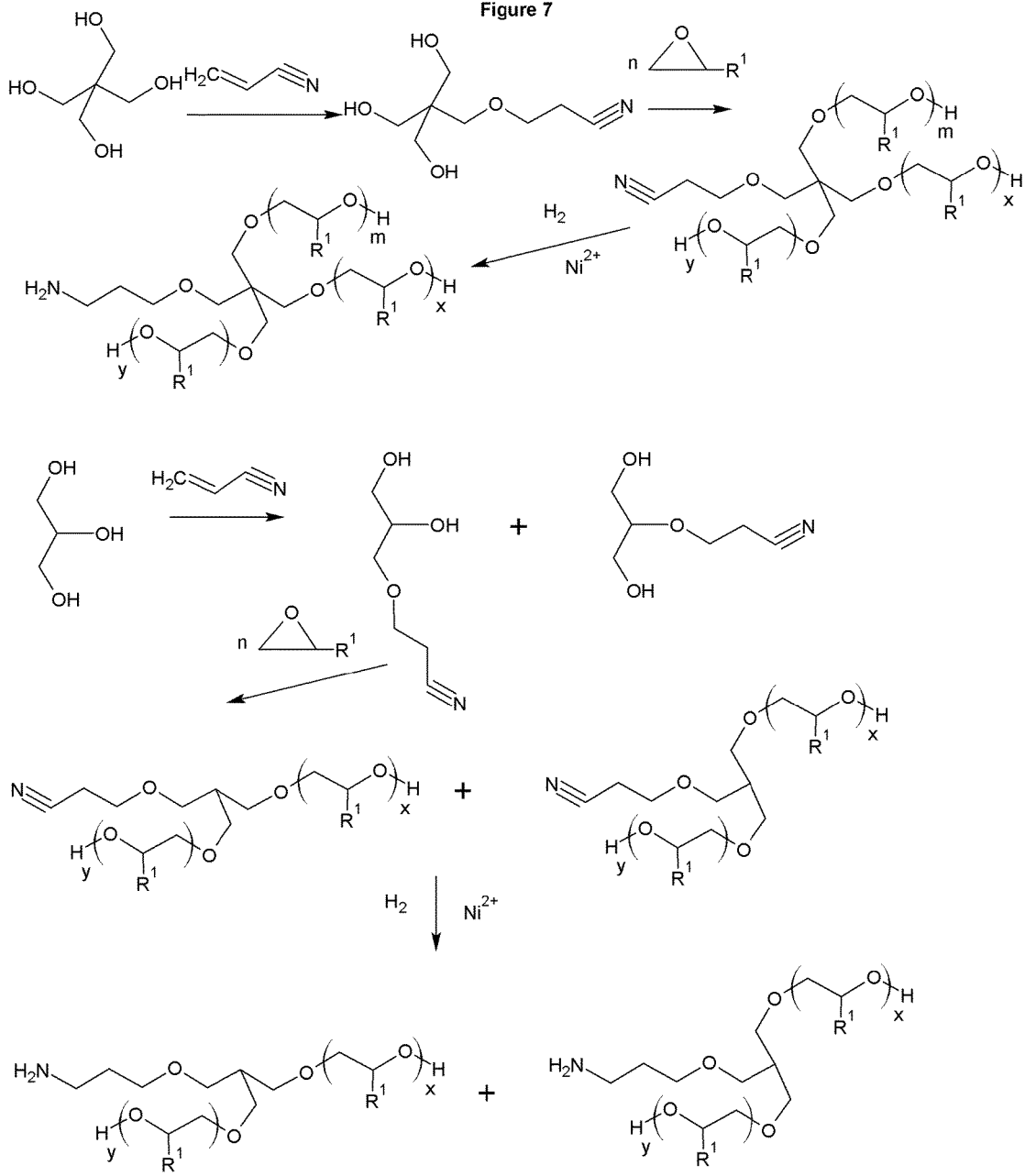
FIG. 7 shows the synthesis of highly branched primary ether amines.

FIG. 7 shows the synthesis of highly branched primary ether amines. The starting materials in FIG. 7 are Pentaerythritol and glycerin, other short chain polyols, such as, but not limited to, neopentyl glycol, ethylene glycol and propylene glycol can be used to obtain the similar analogs. In the cases where multiple products are produced, such as with glycerin, the ether nitriles can be distilled into discreet fractions and then alkoxylated and reduced to obtain more or less discreet products. The range comes from the distribution of alkoxylation then only, not the position of the acrylonitrile addition.

Figure 9:
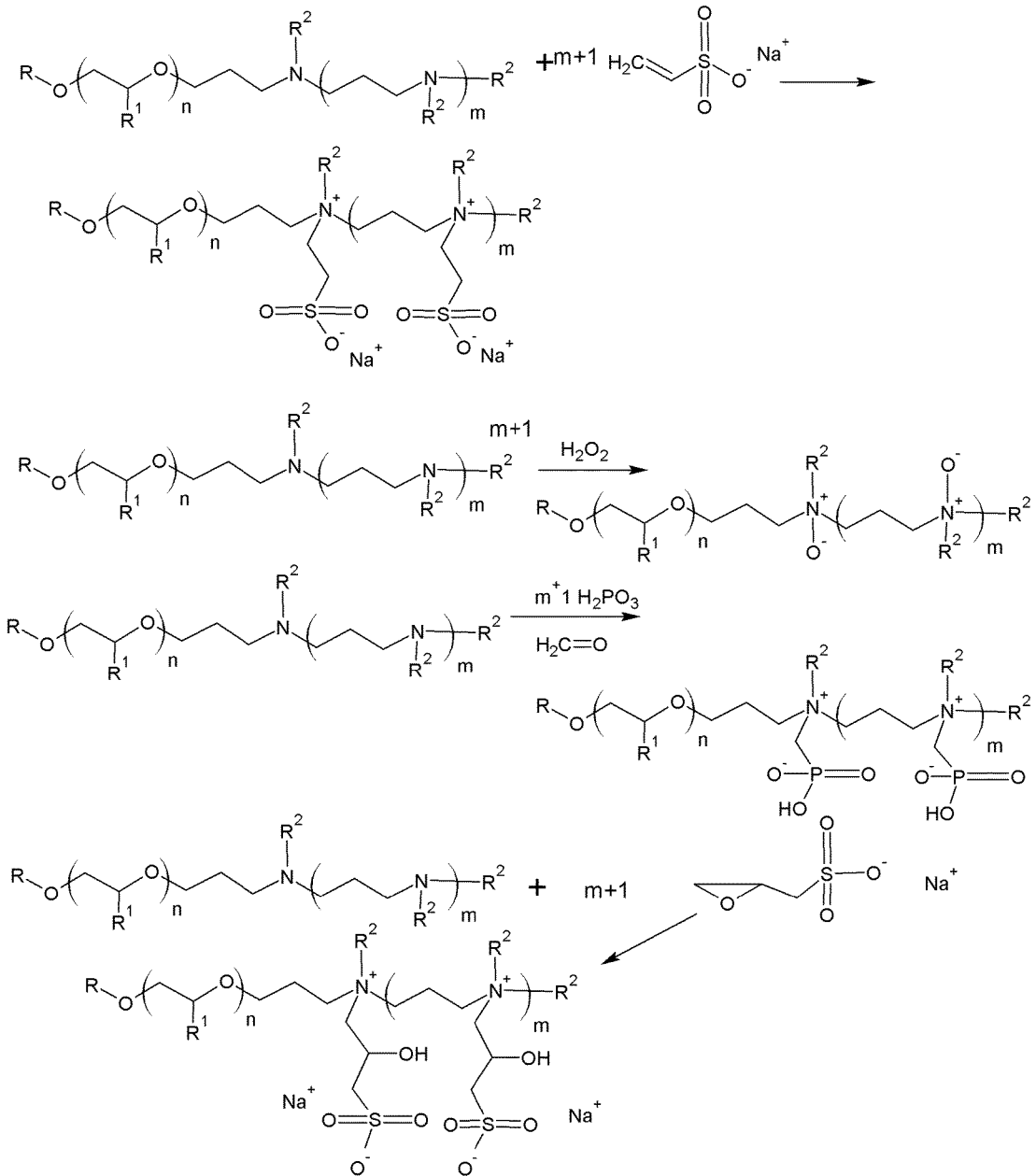

FIGS. 8 and 9 show the synthesis of polyamine derivatives, such as polyquaternaries or polybetaines. The polyquaternaries are shown in the figure to be made with methyl chloride, giving the methyl quats with Cl⁻ anions. Similar to in FIG. 3, other quating agents can be used, including, but not limited to methyl chloride, diethylsulfate, dimethylsulfate, ethyl benzyl chloride, and benzyl chloride. The anions that are generated vary based on the quaternarizing agent, but can also be exchanged through ion exchange to give a wide array of counterions, such as carbonate, borate, phosphate and almost any other anion. Using an epoxide containing agent yields an amphoteric. Further, reactions with alkylating agents that contain an acid group generate betaine surfactants. If asymmetrical tertiary amines are used, the resulting betaines and quaternaries will contain that same asymmetry.

FIG. 10 shows the synthesis of various sulfur derivatives, including the salt free betaines based on sultones. While propane sultone is shown, reacting butane sultone and higher sultones are included as part of this invention, with the resulting betaines having a longer carbon chain between the amine group and the sulfonate group, depending on the sultone. Also shown are the synthesis of novel thionocarbamates. The thionocarbamates are useful as ore collectors for such minerals as gold, copper, zinc, nickel and others minerals.

Figure 11:
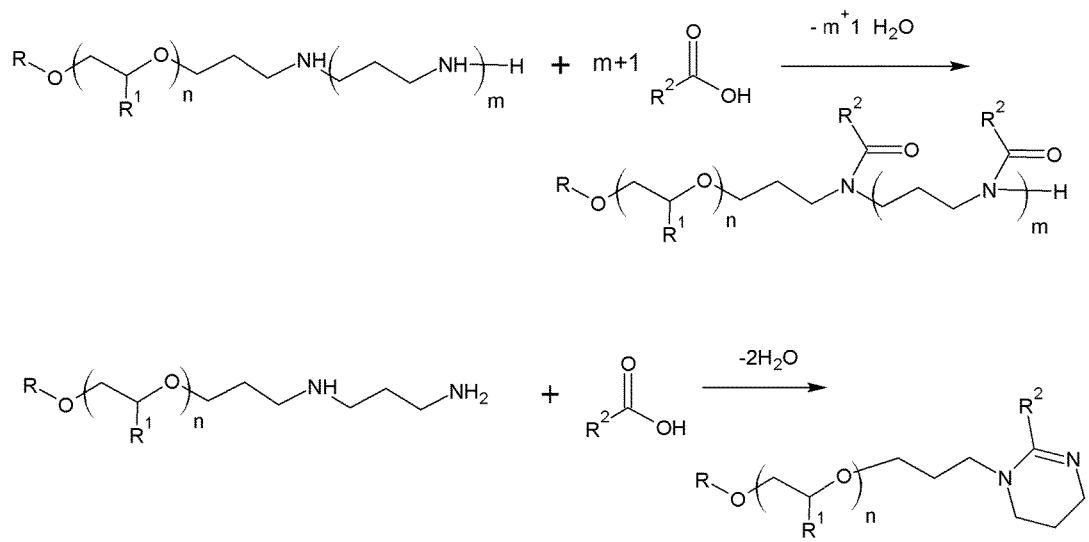
FIG. 11 shows the synthesis of amides and imidazoline analogs.

FIG. 11 shows the synthesis of amides and imidazoline analogs. The Figure shows the synthesis from the diamine, but higher polyamines may also be used, leaving the additional propylamine blocks between the ring and the alcohol that was used to make the polyamine. The imidazoline analogs can also be alkoxylated or quaternized, as described in FIG. 4 or FIG. 6 to alter the water solubility and HLB as desired or to impart cationicity. These products are typically used as corrosion inhibitors, but can be used as lubricity aids and to impart other properties to formulated products. These analogs are part of this invention.

Figure 12:
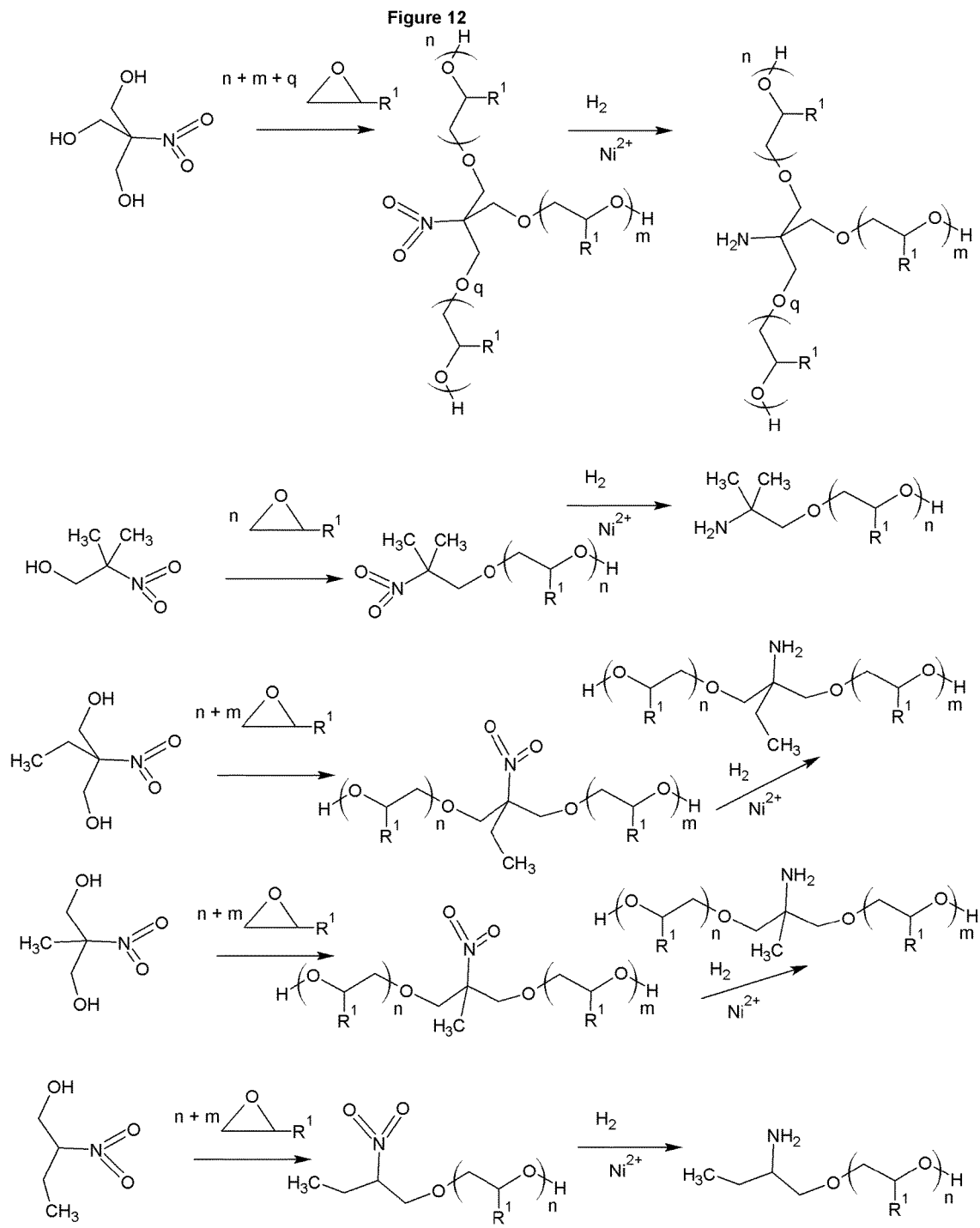
FIGS. 12-13 show the synthesis of a mineral collectors with higher hydrophobicity.

FIG. 12 shows the synthesis of amines based on nitroalcohols. These amines have advantages in the manufacturing and offer a more hydrophobic amine. In the last line of the figure, the alkoxylation must take place with an acid catalyst, or the position of the hydrogen bound to the carbon adjacent to the nitro group will be alkoxylated as in FIG. 13. While the figure shows $R^1$ as a discreet species, it is understood that a mixture of alkoxylating agents could be used to form copolymeric chains among the options for $R^1$. For example, some moles of ethylene oxide could be reacted, followed by some moles of propylene oxide, which would give mixed alkoxylation polymeric chains. The alkoxylation could also take place in one step with various alkoxylating agents added at the same time. The amines present can be reacted with acrylonitrile to make polyamines. The amines in FIG. 12 all have terminal hydroxyls that react with acrylonitrile the same way as the alcohol groups in FIG. 1, either as single cyanoethylation, or sequentially to add polyamines. If the primary amine functionality of the amines in the figure is to be retained, the reaction with acrylonitrile should occur prior to the reduction step. In that case the nitro group will still be reduced when the reduction is performed, along with the nitrile group(s), but the nitro will not react with the acrylonitrile as would the amine if the acrylonitrile is added after the initial reduction. The amines of FIGS. 12 and 13 all have terminal hydroxyls. These can be capped with methyl chloride, or other alkyl halide, prior to reduction from nitro to amine, eliminating the hydroxyl group. The amines of FIG. 12 are preferred to those of FIG. 13 due to the process for manufacturing being safer and the use of formaldehyde to form the nitro alcohol does not add substantial cost.

Similar to FIGS. 1, 2, 3, and 4, the amines in FIG. 5, FIG. 6, FIG. 7, FIG. 12, and FIG. 13 can be derivatized into tertiary amines, amine oxides, quaternaries, sulfonates, sulfates, betaines, betaine esters, phosphonates and alkoxylates. The amine products taught in this invention are used in mineral floatation, either alone or in combination with other known collectors, and or with non-ionic surfactants or other frothing aids, asphalt emulsifiers.

Figure 14:
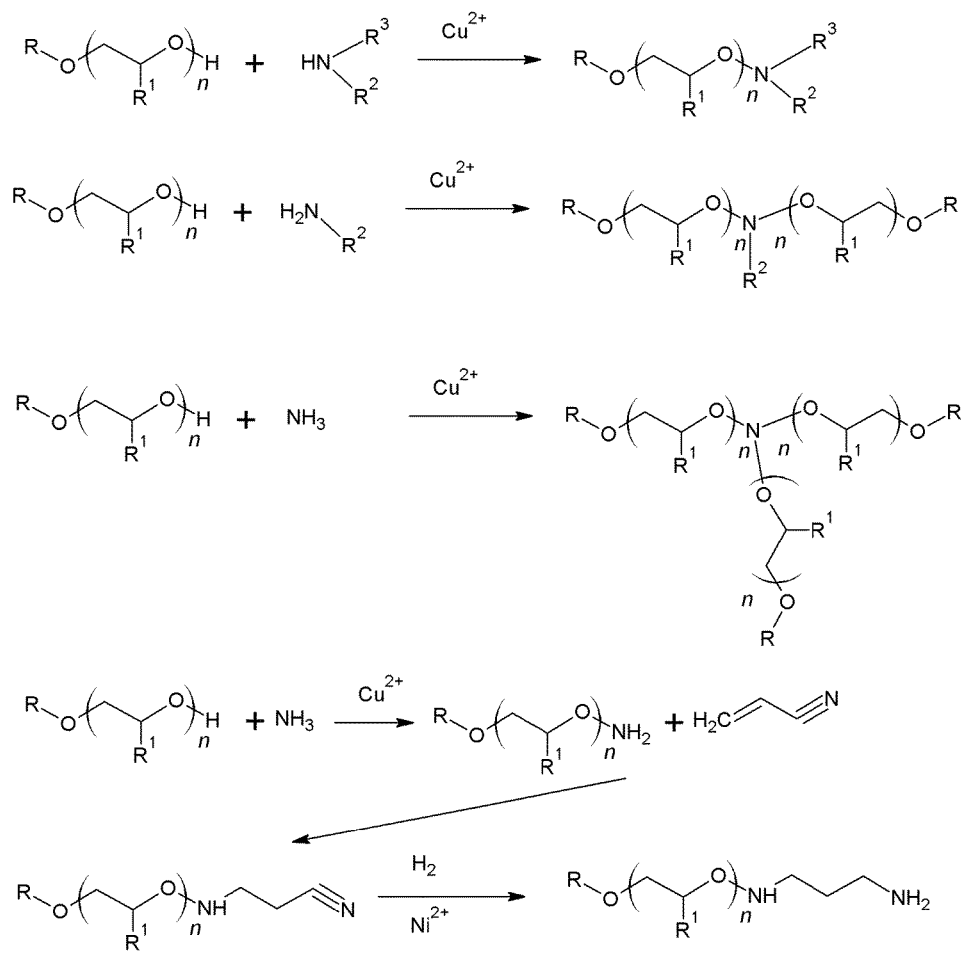
FIG. 14 shows the synthesis of amines via direct amination.

FIG. 14 shows the synthesis of amines via the direct amination route that is most commonly used to make alkyl dimethyl amines (ADMAs). The same route, when properly controlled forms primary, dialkyl or trialkyl amines. The primary amines can similarly be derivatized into polyamines via cyanoethylation as shown in FIG. 1, and sequential cyanoethylation produces the higher polyamines, such as triamines, tetramines, pentamines, and so on. The primary amines and polyamines can also be derivatized into dithiocarbamates, analogous to those in FIG. 2 and amphoterics as shown in FIG. 3. Furthermore, the primary amines and polyamines of FIG. 14 can be alkoxylated with typical alkoxylating agents such as ethylene oxide, propylene oxide and butylene oxide to make particularly useful adjuvants for agriculture or fuel additives that act as detergents. The ethoxylated primary and diamines are particularly well suited as adjuvants in agriculture. This is also the case for the analogous amines and polyamines of FIG. 1. The primary amines and polyamines of FIG. 14 can also be used as starting materials for amphoterics by the reaction with MCA, acrylic acid, methacrylic acid, sodium vinyl sulfonate, sultanes and formaldehyde with phosphorous acid analogous to those shown in FIGS. 3, 8, and 9. The tertiary amines and polyamines of FIG. 14 can be converted to quaternary ammonium compounds and amine oxides that are analogous to those in FIGS. 4 and 6.

Similarly, FIG. 15 shows the tertiary amines and tertiary polyamines can be used as starting materials to produce the analogous betaines of those shown in FIG. 10. In the case of acrylic acid or methacrylic acid being used the variable J is not present, but as an anion of the terminal oxygen. This is the case in FIG. 10 as well. These betaines and polybetaines of FIG. 10 and FIG. 15 are well suited to emulsifying difficult to emulsify asphalt.

Several descriptions and illustrations have been presented to enhance understanding of the present invention. One skilled in the art will know that numerous changes and variations are possible without departing from the spirit of the invention. Each of these changes and variations are within the scope of the present invention.

I claim:

1. An asphalt emulsifier and its relevant salts of the following structure:

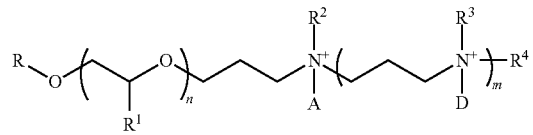

where R is linear or branched, saturated or unsaturated, cyclic or acyclic alkyl group from 1 to 9 carbons, $R^1$ is chosen from —$CH_3$ or —$CH_2CH_3$, $R^2$, $R^3$ and $R^4$ are independently chosen from —H, alkyl, and —$(CH_2CH_2O)_p$H—$(CH(CH_3)CH_2O)_qH$—$(CH(CH_2CH_3)CH_2O)_rH$, and A and D, are independently chosen from alkyl of 1-22 carbon atoms —$CH_2COOH$, —$CH_2CH_2COOH$, —$CH(CH_3)COOH$, —$CH_2$—$C_6H_6$, and O, n is a positive integer, m, p, q and r are non-negative integers; $R^2$ and $R^3$ or A and D need not be present; when A and D or $R^2$ and $R^3$ are not present, then N is not a cation.

2. The asphalt emulsifier and its relevant salts of claim 1 where $R^2$=$R^3$=$R^4$=—H, A and D are not present.

3. The asphalt emulsifier and its relevant salts of claim 1 where $R^2=R^3=R^4=A=D-CH_3$.

4. The asphalt emulsifier and its relevant salts of claim 1 where $R^2$, $R^3$ and $R^4$ are independently chosen from —$(CH_2CH_2O)_pH$—$(CH(CH_3)CH_2O)_qH$—$(CH(CH_2CH_3)CH_2O)_rH$, p, q and r are non-negative integers, A and D are not present.

5. The asphalt emulsifier and its relevant salts of claim 1 where $R^2=R^3=R^4=$—$CH_3$, $A=D=$—$CH_2COOH$.

6. The asphalt emulsifier and its relevant of claim 1 where $R^2=R^3=R^4=$—$CH_3$, $A=D=$—$CH_2CH(CH_3)COOH$.

7. The asphalt emulsifier and its relevant saltst of claim 1 where $R^2=R^3=R^4=$—$CH_3$, $A=D=$—$CH_2CH_2COOH$.

8. The asphalt emulsifier and its relevant salts of claim 1 where $R^2=R^3=R^4=$—$CH_3$, $A=D=$—$O$.

9. The asphalt emulsifier and its relevant saltst of claim 1 where $R^2$, $R^3$ and $R^4$ are independently chosen from —$(CH_2CH_2O)_pH$—$(CH(CH_3)CH_2O)_qH$—$(CH(CH_2CH_3)CH_2O)_rH$, p, q and r are non-negative integers, $A=D=$—$CH_3$.

10. The asphalt emulsifier and its relevant salts of claim 1 where $R^2$, $R^3$ and $R^4$ are independently chosen from —$(CH_2CH_2O)_pH$—$(CH(CH_3)CH_2O)_qH$—$(CH(CH_2CH_3)CH_2O)_rH$, p, q and r are non-negative integers, $A=D=$—$O$.

\* \* \* \* \*